(12) United States Patent
Kuusela et al.

(10) Patent No.: US 10,342,994 B2
(45) Date of Patent: Jul. 9, 2019

(54) METHODS AND SYSTEMS FOR GENERATING DOSE ESTIMATION MODELS FOR RADIOTHERAPY TREATMENT PLANNING

(71) Applicant: VARIAN MEDICAL SYSTEMS INTERNATIONAL AG, Cham (CH)

(72) Inventors: Esa Kuusela, Espoo (FI); Lauri Halko, Helsinki (FI); María Cordero Marcos, Espoo (FI)

(73) Assignee: VARIAN MEDICAL SYSTEMS INTERNATIONAL AG (CH)

( * ) Notice: Subject to any disclaimer, the term of this patent is extended or adjusted under 35 U.S.C. 154(b) by 0 days.

(21) Appl. No.: 15/377,962

(22) Filed: Dec. 13, 2016

(65) Prior Publication Data

US 2018/0161596 A1    Jun. 14, 2018

(51) Int. Cl.
| | |
|---|---|
| *A61N 5/10* | (2006.01) |
| *G06N 20/00* | (2019.01) |
| *G16H 50/20* | (2018.01) |
| *G16H 50/50* | (2018.01) |

(52) U.S. Cl.
CPC ......... *A61N 5/1038* (2013.01); *A61N 5/1031* (2013.01); *G06N 20/00* (2019.01); *G16H 50/20* (2018.01); *G16H 50/50* (2018.01)

(58) Field of Classification Search
None
See application file for complete search history.

(56) References Cited

U.S. PATENT DOCUMENTS

| | | | | |
|---|---|---|---|---|
| 2013/0085343 | A1* | 4/2013 | Toimela | A61N 5/1031 600/300 |
| 2015/0094519 | A1* | 4/2015 | Kuusela | A61N 5/1039 600/1 |
| 2016/0129282 | A1* | 5/2016 | Yin | A61N 5/103 600/1 |
| 2018/0043182 | A1* | 2/2018 | Wu | G16H 50/30 |
| 2018/0165423 | A1 | 6/2018 | Kuusela et al. | |

* cited by examiner

*Primary Examiner* — Whitney Moore
(74) *Attorney, Agent, or Firm* — Su IP Consulting (57) ABSTRACT

One example method for generating a dose estimation model for radiotherapy treatment planning may include obtaining training data that includes multiple treatment plans associated with respective multiple past patients. The method may also include processing the training data to determine, from each of the multiple treatment plans, first data that includes one or more features associated with a particular past patient, second data associated with treatment planning trade-off selected for the particular past patient and third data associated with radiation dose for delivery to the particular past patient. The method may further include generating the dose estimation model by training, based on the first data, second data and third data from the multiple treatment plans, the dose estimation model to estimate a relationship that transforms the first data and second data to the third data.

21 Claims, 6 Drawing Sheets

METHODS AND SYSTEMS FOR GENERATING DOSE ESTIMATION MODELS FOR RADIOTHERAPY TREATMENT PLANNING

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, in practice, there are various challenges associated with radiotherapy treatment planning to deliver radiation doses that achieve this goal.

SUMMARY

In accordance with some embodiments of the present disclosure, example methods and systems for generating a dose estimation model for radiotherapy treatment planning are provided.

In one embodiment, the method may comprise: obtaining training data that includes multiple treatment plans and processing the training data to determine, from each of the multiple treatment plans, first data associated with patient geometry, second data associated with treatment planning trade-off and third data associated with radiation dose. The method may further comprise: using the first data, second data and third data from the multiple treatment plans, training the dose estimation model to estimate a relationship that transforms the first data and second data to the third data.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
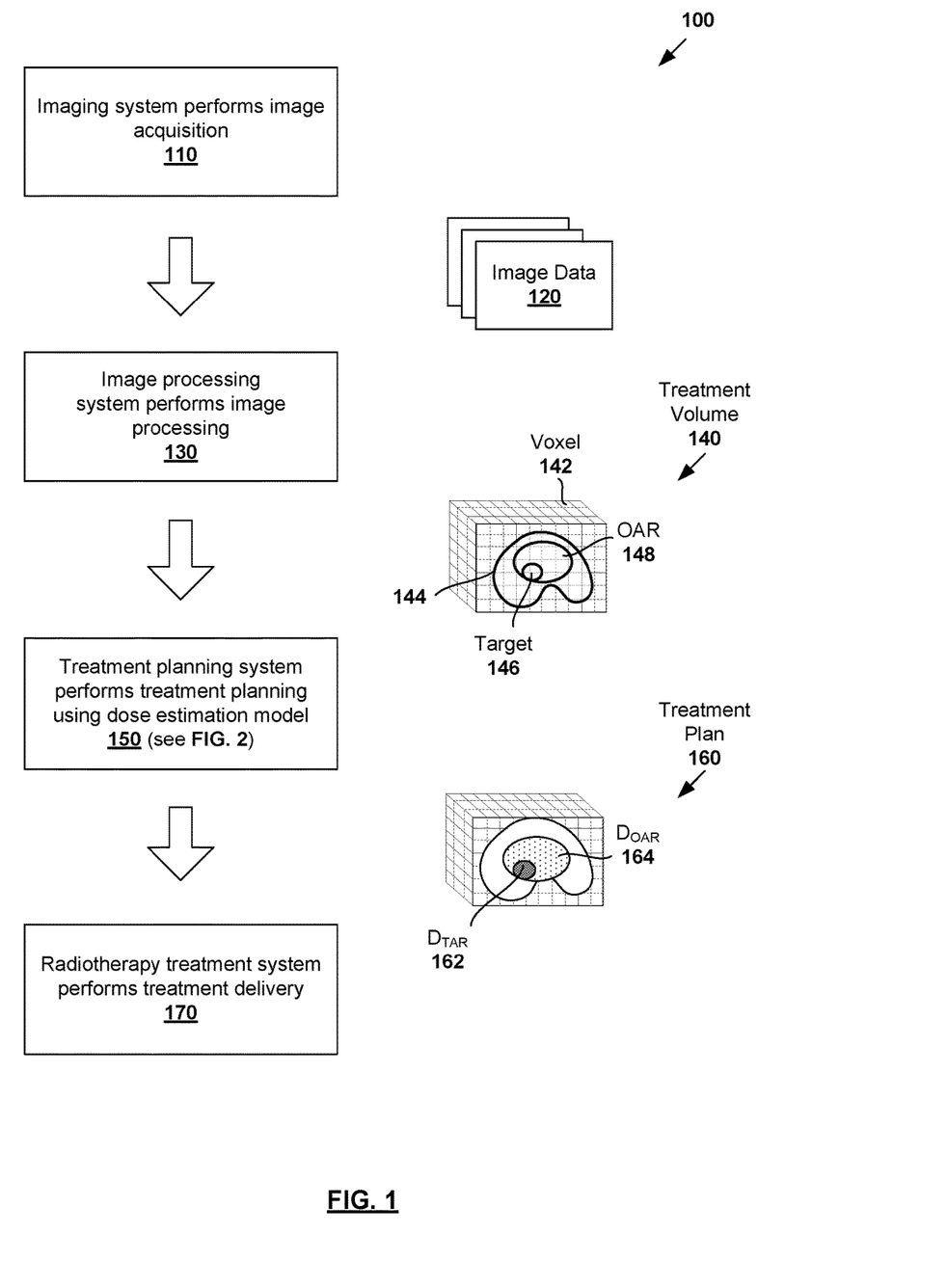
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks, such as 110 to 170. The various blocks may be combined into fewer blocks, divided into additional blocks, and/or eliminated based upon the desired implementation. In the example in FIG. 1, radiotherapy treatment generally includes various stages, such as image data acquisition performed by an imaging system (see 110-120); image processing by an image processing system (see 130-140); treatment planning by a treatment planning system (see 150-160); and treatment delivery by a radiotherapy treatment system (see 170).

As will be further described below, treatment planning (see 150 in FIG. 1) may be improved according to examples of the present disclosure to facilitate better treatment delivery. For example, given the often close proximity between tumors and proximal healthy structures (e.g., organs, etc.), any improvement in treatment planning has the potential of improving treatment outcome, such as increasing the tumor control probability and/or reducing the likelihood of minor through severe health complications or death due to radiation overdose in the healthy structures.

At 110 in FIG. 1, image data acquisition is performed using an imaging system to capture image data 120 of a patient's anatomy requiring radiotherapy treatment. Any suitable imaging modality or modalities may be used by the imaging system, such as computed tomography (CT), positron emission tomography (PET), magnetic resonance imaging (MRI), single photon emission computed tomography (SPECT), etc. When CT or MRI is used, image data 120 may include a series of two-dimensional (2D) images or slices, each representing a cross-sectional view of the patient's anatomy.

At 130 in FIG. 1, image processing is performed to process image data 120 using an image processing system, such as to reconstruct a three-dimensional (3D) volume of the patient's anatomy from image data 120. The 3D volume is known as "treatment volume" 140 that will be subjected to radiation. Treatment volume 140 may be divided into multiple smaller volume-pixels (voxels), each voxel representing a 3D element associated with location (i, j, k) within treatment volume 140. At this stage, information that is useful for subsequent treatment planning 150 may be extracted from treatment volume 140, such as data relating to the contour, shape, size and location of patient's anatomy 144, target 146 and any organ-at-risk (OAR) 148.

In practice, target 146 may represent a malignant tumor (e.g., prostate tumor, etc.) requiring radiotherapy treatment, and OAR 148 a proximal healthy structure (e.g., rectum, bladder, etc.) that might be adversely affected by the treatment. Target 146 is also known as a planning target volume (PTV), and treatment volume 140 as an irradiated volume. Although an example is shown in FIG. 1, treatment volume 140 may include multiple targets 146 and OARs 148 with complex shapes and sizes in practice. Further, although shown as having a regular shape (e.g., cube), voxel 142 may have any suitable shape (e.g., non-regular).

At 150 in FIG. 1, treatment planning is performed using a treatment planning system to determine treatment plan 160. For example in FIG. 1, treatment plan 160 specifies radiation dose for target 146 (denoted "$D_{TAR}$" at 162) and radiation dose for OAR 148 (denoted "$D_{OAR}$" at 164).

At 170 in FIG. 1, treatment delivery 170 is performed using a radiotherapy treatment system to deliver radiation to the patient according to treatment plan 160. In practice, treatment planning may be performed based on goal doses prescribed by a clinician (e.g., oncologist, dosimetrist, treatment planner, etc.), such as based on the clinician's experience, the type and extent of the tumor at target 146, patient geometry and condition, etc.

An important aspect of treatment planning 150 is estimating the level of radiation dose to be applied to the patient. In practice, knowledge-based treatment planning may be used, in which achievable doses for target 146 and OAR 148 are estimated based on existing clinical knowledge. This involves training a "dose estimation model" (also known as "dose prediction model") using a set of treatment plans (also known as "training data") previously devised for past patients. Ideally, the training data should be of high quality, and sufficiently similar to a treatment being planned for a new patient (e.g., similar treatment area, etc.). Once trained, the dose estimation model may be used to automatically determine treatment plan 160 for the new patient.

Conventionally, a dose estimation model contains rules to transform patient geometry data (i.e., known prior to optimization and called "independent data") into dosimetrical data (i.e., known after the optimization and called "dependent data"). When used with an optimization algorithm, estimates produced by the dose estimation model may be optimized according to optimization objectives set by the clinician to produce complete treatment plan 160. However, in practice, it is not always clear what "optimality" refers to.

For example, in intensity-modulated radiation therapy (IMRT), OAR dose level (see $D_{OAR}$ 164) may be reduced by accepting a looser conformity with target dose level (see $D_{TAR}$ 162). In case of multiple OARs, the dose level for one OAR may be reduced by accepting a higher dose to another OAR. The resulting "optimal" dose distribution therefore reflects, to a certain extent, the preferences of the clinician, which in turn might reflect at least partly the additional knowledge the clinician has from the patient. Also, the objective set by the clinician might cause some arbitrariness to the "optimal" dose distribution.

For the above reasons, the training data for training a dose estimation model may have additional variation due to somewhat different criteria that cannot be explained by considering the patient geometry data alone. This may cause several problems in practice. In one example, the additional variation might increase unexplained variance of the dose estimation model, thereby making dose estimations less accurate. In another example, treatment plans that have significantly different trade-off (e.g., between OAR dose level and target coverage) are considered outliers, and additional work is required to remove such outliers from the training data.

Ideally, a clinician should be able to recognize treatment plans with trade-offs and exclude them from the training data (usually performed manually). However, it is not always straightforward to identify such treatment plans. For example, treatment plans that appear to have the same goals might rely on different trade-offs between objectives. To identify such treatment plans, a comparison between a dose specified in a treatment plan used for training, and a dose estimated by the resulting dose estimation model is required. For example, the treatment plan may specify a significantly lower dose than the dose estimation model is predicting in one OAR, but a significantly higher dose than the model is predicting in another OAR. This suggests that the treatment plan relies on a non-canonical balance between the sparing of these two OARs, and should be removed.

Even when the above treatment plans are successfully identified and excluded from the training data, their exclusion might present another problem. In particular, once the treatment plans are removed, the scope of the resulting dose estimation model would be reduced because it cannot be applied in situations with treatment planning trade-offs. If the clinician prefers improved target dose conformity in certain cases, this will not be understood by the dose estimation model.

Dose Estimation Model with Treatment Planning Trade-Off

According to examples of the present disclosure, radiotherapy treatment planning may be improved using a dose estimation model that takes into account treatment planning trade-off. Instead of necessitating the removal of certain treatment plans that are considered to be outliers, the training data may include such outliers to train a more flexible dose estimation model. This way, for example, the training data may be used more freely and the trade-off between various objectives may be considered using the same dose estimation model.

Figure 2:
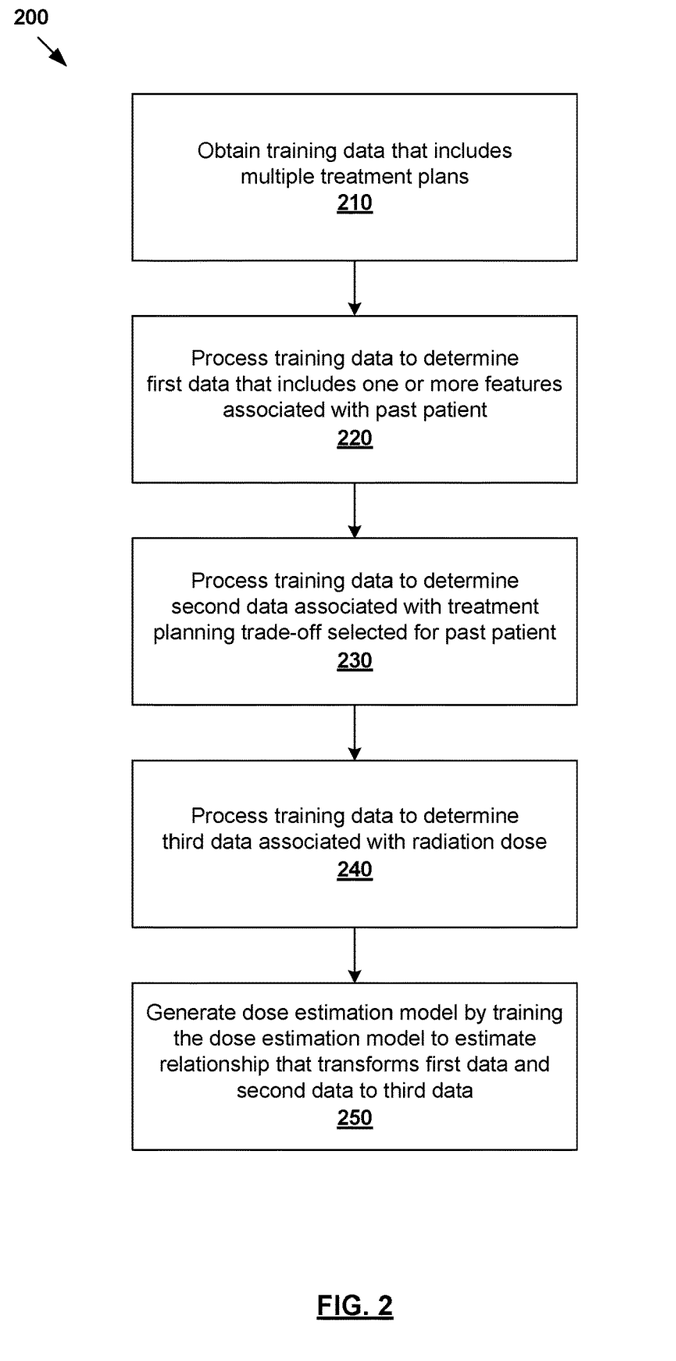
FIG. 2 is a flowchart of an example process for a computer system to generate a dose estimation model for radiotherapy treatment planning.

In more detail, FIG. 2 is a flowchart of example process 200 for a computer system to generate a dose estimation model for radiotherapy treatment planning. Example process 200 may include one or more operations, functions, or actions illustrated by one or more blocks, such as 210 to 250. The various blocks may be combined into fewer blocks, divided into additional blocks, and/or eliminated based upon the desired implementation. Example process 200 may be implemented using any suitable computer system, an example of which will be discussed using FIG. 6.

At 210 in FIG. 2, training data that includes multiple treatment plans associated with respective multiple past patients are obtained. Here, the term "obtain" may refer generally to retrieving the training data from any suitable storage (e.g., database of historical treatment plans) accessible by the computer system, receiving the training data from another source via any suitable communication link, etc.

At 220 in FIG. 2, the training data is processed to determine, from each of the multiple treatment plans, first data that includes one or more features associated with a particular past patient. For example, the first data may include one or more features associated with patient geometry, such as target volume, OAR volume, relative overlap volume (i.e., fraction of target volume overlapping with OAR volume), relative out-of-field volume (i.e., fraction of target or OAR volume outside of the treatment field), distance to target (DTH) values that expresses the distance from a region or structure such as OAR 148 from target 146, etc. Any other suitable first data may be used in practice.

At 230 in FIG. 2, the training data is processed to determine, from each of the multiple treatment plans, second data associated with treatment planning trade-off selected for the particular past patient. As used herein, the term "trade-off" may refer generally to a balance between two treatment objectives (e.g., between "first objective" and "second objective") during radiotherapy treatment planning, which may be both desirable but competing with each other.

The second data may include one or more dosimetrical features associated with the first objective or second objective, such as OAR dose level (e.g., mean dose, median dose, maximum dose, minimum dose, etc.), relative target volume with a particular prescribed dose or higher, desired normalization volume for 98% dose level (or any other suitable level), etc. Alternatively or additionally, the second data may include one or more non-dosimetrical features associated with the first objective or second objective, such as Monitor Unit (MU), deviation of MU from an average value, treatment time, machine-related feature(s) of a radiotherapy treatment system (see FIG. 6), etc. As will be discussed further using FIG. 3, it should be understood that the trade-off may be one-to-one, one-to-many, or many-to-many.

At 240 in FIG. 2, the training data is processed to determine, from each of the multiple treatment plans, third data associated with radiation dose for delivery to the particular past patient. The third data may include one or more features associated with radiation dose, such 3D dose distribution, dose-volume histograms (DVH), etc. In general, a 3D radiation dose distribution defines the magnitude of radiation at each voxel representing target 146 or OAR 148. 3D dose distributions may be summarized using dose-volume histograms (DVH) in a 2D format. Radiation dose may be measured in Gray (Gy), which represents the absorption of one joule of radiation energy in one kilogram of matter.

At 250 in FIG. 2, a dose estimation model is generated by training, based on the first data, second data and third data from the multiple treatment plans, the dose estimation model to estimate a relationship that transforms the first data and second data to the third data. In one example, the generated dose estimation model expresses radiation dose (i.e., dependent third data) as a function of patient geometry and treatment planning trade-off (i.e., independent first and second data). As will be described further using FIG. 4, once trained using the multiple treatment plans devised for different patients, the dose estimation model may be used to predict or estimate radiation dose for a particular patient.

In the following, various examples will be discussed using FIG. 3 to FIG. 6. In particular, example dose estimation model training will be discussed using FIG. 3, example treatment planning using FIG. 4 and FIG. 5, and example computer system and radiotherapy system using FIG. 6.

Dose Estimation Model Training

Figure 3:
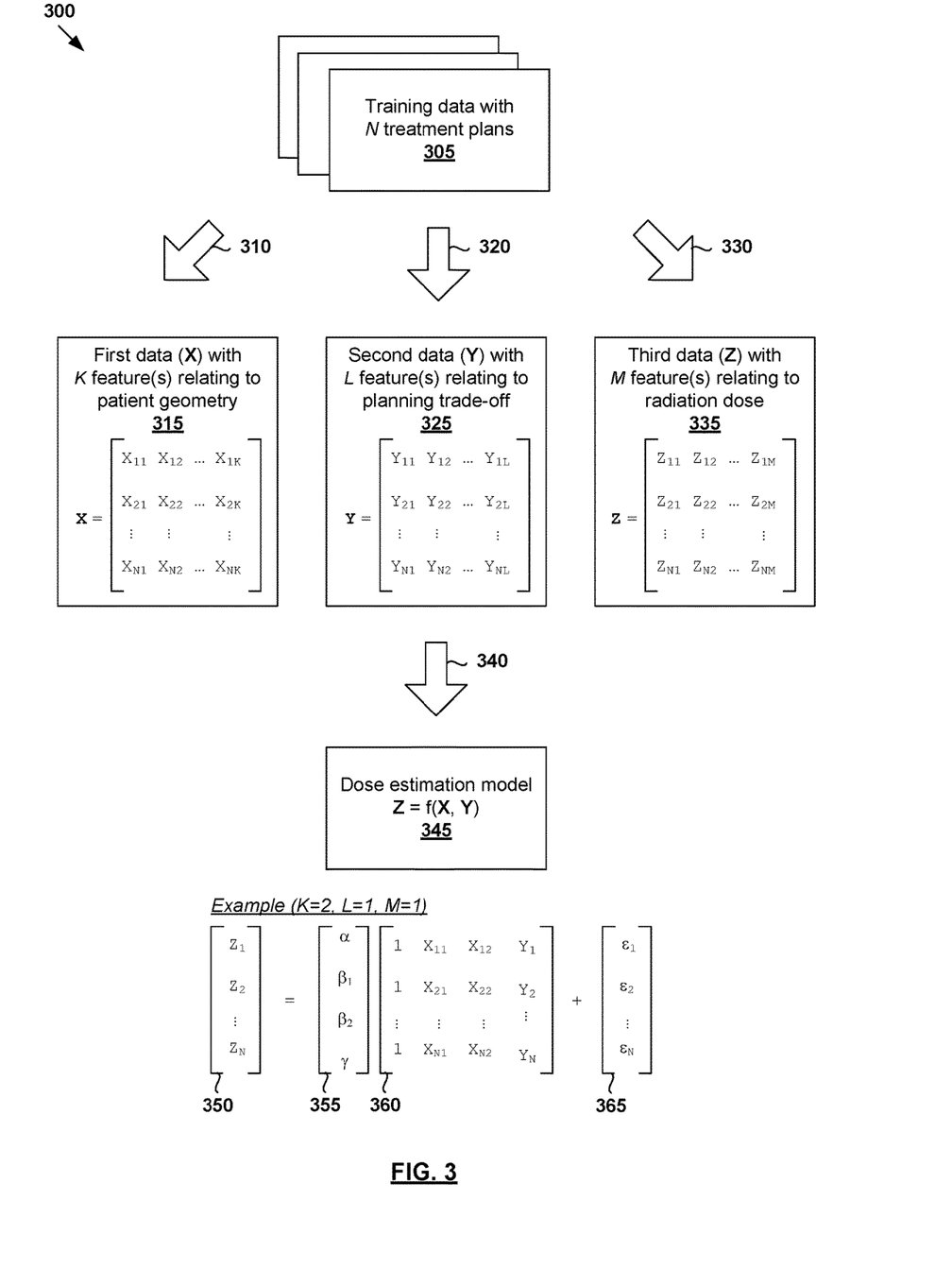
FIG. 3 is a schematic diagram illustrating an example process for a computer system to train a dose estimation model for radiotherapy treatment planning.

FIG. 3 is a schematic diagram illustrating example process 300 for a computer system to train a dose estimation model for radiotherapy treatment planning. Example process 300 may include one or more operations, functions, actions or data items illustrated by one or more blocks, such as 310 to 365. The various blocks may be combined into fewer blocks, divided into additional blocks, and/or eliminated based upon the desired implementation. Similar to the example in FIG. 2, example process 200 may be implemented using any suitable computer system, an example of which will be discussed using FIG. 6.

Example process 300 may be implemented to train a dose estimation model for any suitable radiotherapy treatment planning, such as relating to cancer treatment, etc. For example, in relation to lung cancer, target 146 represents cancerous lung tissue, and OAR 148 may be proximal healthy lung tissue, esophagus, heart, etc. In relation to prostate cancer, target 146 represents a patient's prostate, and OAR 148 a proximal healthy structure such as rectum, bladder, etc. In the following, an example will be described in relation to prostate cancer.

Referring first to 305 in FIG. 3, training data that includes N treatment plans associated with respective multiple past patients is obtained, such as by retrieving from a database of past treatment plans, receiving from another computer system via a communication link, etc. The training data may be obtained based on their relevance to a particular treatment area, such as prostate in the example below. A particular treatment plan in training data 305 may be denoted as the $i^{th}$ treatment plan, where $i=1, \ldots, N$.

At 310, 320 and 330 in FIG. 3, training data 305 is processed to determine various data (see "first data" 315, "second data" 325, "third data" 335) required to train the dose estimation model. Here, the term "process" or "processing" may include any suitable data processing operation(s), such as data analysis, feature extraction, calculation, derivation, transformation, any combination thereof, etc. First data 315 and second data 325 represent the input or "independent" variables of the dose estimation model, while third data 335 represents the output or "dependent" variables.

Prior to the processing at 310, 320 and 330 in FIG. 3, a clinician may select specific parameter(s) or feature(s) of first data 315, second data 325 and third data 335 to be determined from training data 305. For example, the feature(s) may be selected or entered via a graphical user interface (GUI) provided by the computer system, etc. The specific feature(s) may depend on the clinician's experience and knowledge, type of radiotherapy treatment required, beam configuration (e.g., energy, collimator size and orientations), etc. The clinician may also rely on any expertise or knowledge relating to the biological effect of radiation on target 146 and/or OAR 148, such as based on tumor control probability, normal tissue complication probability, etc. The tumor control probability is the probability of eradicating all tumor cells as a function of dose. The normal tissue complication probability is the probability of, as a function of dose, inducing some particular complication (a collective word for describing a variety of conditions such as nausea, vomiting, etc.) in a normal organ.

At 310 in FIG. 3, training data 305 is processed to determine first data 315 that includes $K \geq 1$ feature(s) associated with patient anatomy. First data 315 may be represented using a N×K matrix denoted as X, and feature(s) from the $i^{th}$ treatment plan may be represented as $X_i=(X_{i1}, \ldots, X_{iK})$, $i=1, \ldots, N$. In practice, first data 315 may include any suitable patient geometrical or anatomical feature(s) that can be extracted or derived from training data 305, such as target volume; OAR volume; relative volume; relative out-of-field volume, etc. Distance to target histograms (DTHs) that measure the distance from particular target 146 may also be derived from training data 305.

At 320 in FIG. 3, training data 305 is processed to determine second data 325 that includes $L \geq 1$ feature(s) associated with treatment planning trade-off. Second data 325 may be represented using a N×L matrix denoted as Y, and feature(s) from the $i^{th}$ treatment plan may be represented as $Y_i=(Y_{i1}, \ldots, Y_{iL})$, $i=1, \ldots, N$. For example, in the case of L=1, $Y_i$ is a 1D vector with a singular value $Y_i$. In practice, second data 325 may be associated with a treatment planning trade-off between a first objective and a second objective. The first objective or second objective may be parameterized using any suitable dosimetrical and/or non-dosimetrical feature(s) that can be extracted or derived from training data 305.

According to examples of the present disclosure, any suitable treatment planning trade-off between a first objective and a second objective may be considered. The trade-off may be one-to-one, one-to-many, or many-to-many. Some examples will be discussed below.

(a) In a first example, a one-to-one trade-off may be between a first objective associated with OAR 148 (e.g., rectum) and a second objective associated with target 146 (e.g., prostate). In this case, the first objective may relate to dose sparing of OAR 148, and the second objective may relate to better target coverage or better target dose conformity. In this example, the second data may include one or more dosimetrical features, such as relative target volume with a particular prescribed dose or higher, desired normalization volume for 98% dose level (or any other suitable level), etc. Dose sparing of OAR 148 may be characterized using OAR dose level, such as mean dose, median dose, maximum dose, minimum dose, etc.

(b) In a second example, a one-to-one trade-off between a first objective associated with a first OAR (e.g., rectum) and a second objective associated with a second OAR (e.g., bladder) to consider dose sparing of multiple OARs. In this example, the second data may include one or more dosimetrical features, such as a ratio between a mean dose of the first OAR and a mean dose of the second OAR; a ratio between a maximum dose of the first OAR and mean dose of the second OAR; etc.

(c) In a third example, a one-to-many trade-off may be between a first objective associated with target 146 (e.g., prostate) and a second objective associated with multiple OARs (e.g., rectum and bladder). In this case, the first objective may relate to better target coverage or better target dose conformity, and the second objective may relate to combined dose sparing of the multiple OARs. Similar to the first example, the first objective may be represented using a relative target volume with a particular prescribed dose or higher, desired normalization volume for 98% dose level (or any other suitable level), etc. Combined dose sparing may be represented using a combined dose level (e.g., mean dose) of the multiple OARs.

(d) In a fourth example, a one-to-one trade-off may be between a first objective associated with a first feature that is non-dosimetrical, and a second objective associated with a second feature (dosimetrical or non-dosimetrical). For example, the first feature may be MU, which measures a machine output from an accelerator of the radiotherapy system, such as a linear accelerator (LINAC), etc. In this example, the second data may include a deviation of MU from an average value (e.g., "normal MU level"=500). In practice, MUs may be in the order of few hundred to a thousand when calibrated in a traditional way, but in principle this is a parameter with free scaling. A higher MU may be used to improve one OAR, while keeping the dose in others roughly the same. The second data may indicate 'more MU(s) than normal' (i.e., positive deviation) or 'less MU(s) than normal' (i.e., negative deviation).

(e) In a fifth example, a one-to-many trade-off may be between a first objective associated with a first feature that is non-dosimetrical, and a second objective associated with multiple second features (dosimetrical, non-dosimetrical, or a combination of both). Using MU as an example, a higher MU may be utilized to improve the overall treatment plan. In this case, similar to the fourth example, the second data may include the deviation of a Monitor Unit (MU) from an average value (e.g., MU=500). Although MU has been used as an example, any other suitable non-dosimetrical feature may be considered, such as treatment time, etc.

(f) An extension to the above examples is a many-to-many trade-off between a first objective associated with a first group of features and a second objective associated with a second group of features. In this case, the second data may include a combined value (e.g., mean dose) representing the first group or second group. The features in each group may be dosimetrical, non-dosimetrical, or a combination of both.

At 330 in FIG. 3, training data 305 is processed to determine third data 335 that includes $M \geq 1$ feature(s) associated with radiation dose to be delivered. Third data 335 may be represented using a N×M matrix denoted as Z. Feature(s) from the $i^{th}$ treatment plan may be represented using $Z_i=(Z_{i1}, \ldots, Z_{iM})$, $i=1, \ldots, N$. For example, in the case of M=1, $Z_i$ is a 1D vector with a singular value $Z_i$. In practice, radiation dose may be specified using dose distribution, DVH, etc.

At 340 in FIG. 3, dose estimation model 345 is trained using (X, Y, Z) to estimate a relationship that transforms independent data (X, Y) to dependent data Z. For example, the relationship or interdependency may be expressed using any suitable function $f(\ )$ as follows:

$$Z=f(X,Y).$$

Any suitable algorithm may be used to estimate function $f(\ )$, such as regression algorithm (e.g., stepwise multiple regression, linear regression, polynomial regression, etc.) to estimate a set of coefficients that transform (X, Y) to Z. It should be understood that any additional and/or alternative algorithm may be used to train the dose estimation model, such as principal component analysis (PCA) algorithm, classification algorithm, clustering algorithm, machine learning algorithm (e.g., supervised learning, unsupervised learning), etc.

For simplicity, consider an example with K=2, L=1 and M=1 in FIG. 3. In this case, first data 315, second data 325 and third data 335 from the $i^{th}$ treatment plan may be expressed as $(X_i, Y_i, Z_i)=(X_{i1}, X_{i2}, Y_i, Z_i)$, where $i=1, \ldots, N$. In relation to prostate cancer treatment planning, target 146 may be a patient's prostate and OAR 148 the rectum. For example, dose estimation model 345 may be designed to take into account the treatment planning trade-off between higher mean dose in rectum (i.e., first objective) and better target coverage (i.e., second objective). In this case, $X_{i1}$=rectum volume; $X_{i2}$=closest distance between rectum and prostate; $Y_i$=relative target volume covered by a dose prescription level and $Z_i$=mean dose on rectum.

Function $f(\ )$ may be presented as a multiplication of combined X and Y (see 360 in FIG. 3) with a matrix of coefficients (see 355 in FIG. 3). In the example in FIG. 3, $\varepsilon_i$ represents the difference (see 356 in FIG. 3) between $Z_i$ (see 350 in FIG. 3) derived from training data 305 and $f(X_{i1}, X_{i2}, Y_i)$ estimated by the model. For example, assuming $f(\ )$ is linear, linear regression may be used to estimate the following dose estimation model:

$$Z_i=\alpha+\beta_1 X_{i1}+\beta_2 X_{i2}+\gamma Y_i+\varepsilon_i.$$

In the above equation, $\beta_1$, $\beta_2$ and $\gamma$ are known as the coefficients associated with respective independent features $X_{i1}$, $X_{i2}$ and $Y_i$; and $\alpha$ is also known as the intercept. In general, $\alpha$, $\beta_1$, $\beta_2$ and $\gamma$ are dimensionless units. To estimate $f(\ )$, values of $(\alpha, \beta_1, \beta_2, \gamma)$ that best fit training data 305 are calculated, such as by minimizing the least-squared errors $\varepsilon^2=(f(X, Y)-Z)^2$.

In practice, training dose estimation model 345 may involve estimating a relationship $\hat{Y}=h(X)$ between first data 315 and second data 325 before adding, to the final dose estimation model 345, a difference (i.e., $Y-\hat{Y}$) between the actual Y in training data 305 and the predicted $\hat{Y}$. In this case, dose estimation model 345 may be expressed as:

$$Z_i = \alpha + \beta_1 X_{i1} + \beta_2 X_{i2} + \gamma(Y_i - \hat{Y}_i) + \varepsilon_i.$$

In a simple example shown in FIG. 3, assuming $\alpha=0$, $\beta_1=2.3$, $\beta_2=-0.7$, $\gamma=3.5$ and $\hat{y}=0.95$ (e.g., average value of $Y_i$ in the training data) are calculated based on training data 305, dose estimation model 345 may be expressed using the equation below. Note that parameters $x_1$=rectum volume; $x_2$=closest distance between rectum and prostate; y=relative target volume covered by a dose prescription level; and z=mean dose on rectum.

$$z = 2.3x_1 - 0.7x_2 + 3.5(y - 0.95).$$

The above model allows a clinician to take into account the treatment planning trade-off between better target coverage (modelled using y) and higher mean dose in rectum (modelled using z). For example, if rectum sparing is preferred, y may be set to a value that is lower than $\hat{y}=0.95$ (i.e., y<0.95), which results in a lower value of z. Otherwise, if better target coverage is preferred, y may be set to a value that is higher than $\hat{y}=0.95$ (i.e., y>0.95), which results in a higher value of z.

By comparison, a conventional dose estimation model does not take into account any treatment planning trade-off. Using the same patient geometrical features $x_1$ and $x_2$, the conventional model may be represented as follows:

$$z_0 = f_0(x_1, x_2) = 2.3x_1 - 0.7x_2.$$

In the above conventional model, $z_0 = f_0(x_1, x_2)$ may be interpreted as the estimated radiation dose given $x_1$ and $x_2$, under the assumption that all other treatment parameters are following the training data distribution.

In contrast, according to examples of the present disclosure, $z = f(x_1, x_2, y)$ may be interpreted as the estimated radiation dose given $x_1$ and $x_2$, under the assumption that y deviates from the training data distribution. In at least some examples, the sum of squared differences between z and Z is expected to be smaller than or equal to the same quantity calculated over $z_0$, i.e., $(z-Z)^2 \leq (z_0-Z)^2$ or $(f(x_1, x_2, y) - Z)^2 \leq (f_0(x_1, X_2) - Z)^2$.

Treatment Plan Generation and Treatment Delivery

Figure 4:
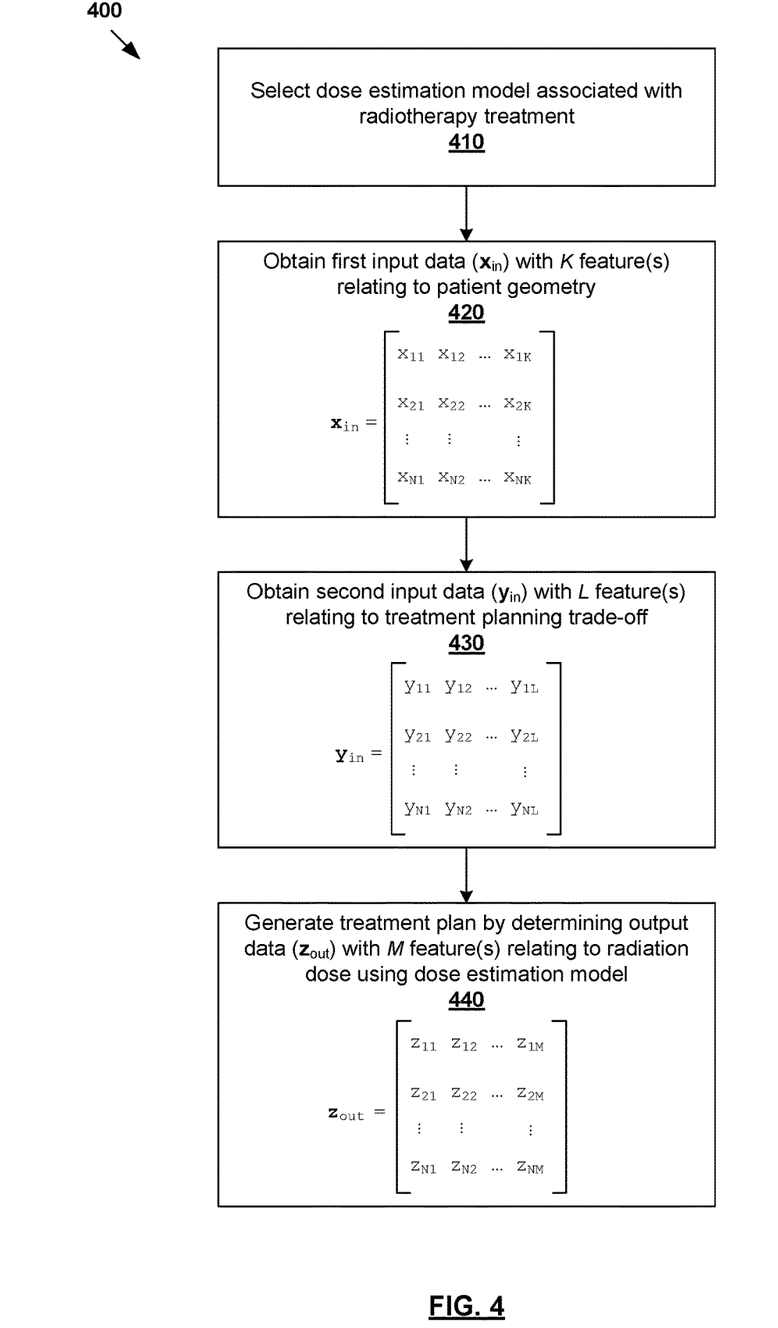
FIG. 4 is a flowchart of an example process for a computer system to automatically generate a treatment plan based on the dose estimation model trained according to the example process in FIG. 3.

FIG. 4 is a flowchart of example process 400 for a computer system to automatically generate a treatment plan based on the dose estimation model trained according to example process 300 in FIG. 3. The various blocks may be combined into fewer blocks, divided into additional blocks, and/or eliminated based upon the desired implementation. Similar to the example in FIG. 2, example process 200 may be implemented using any suitable computer system, an example of which will be discussed using FIG. 6.

At 410 in FIG. 4, a dose estimation model is selected for the radiotherapy treatment planning of a particular patient. In practice, example process 300 in FIG. 3 may be repeated to determine multiple dose estimation models from a single set of training data 305, or multiple sets of training data 305. The dose estimation may be selected based on any suitable factor(s), such as a treatment region of the patient, a treatment planning trade-off preferred by the clinician, etc.

At 420 and 430 in FIG. 4, first input data $x_{in}$ relating to patient geometry of the particular patient, and second input data $y_{in}$ relating to treatment planning trade-off are obtained. In practice, first input data $x_{in}$ and second input data $y_{in}$ may be "obtained" using any suitable approach, such as received via a GUI provided by the computer system, retrieved from storage, derived from other inputs (e.g., "instruction" discussed below), etc. Using the example in FIG. 3, $x_{in}$ is a 2D vector $(x_1, x_2)$ and $y_{in}=y$, where $x_1$=rectum volume of the patient; $x_2$=closest distance between the patient's rectum and prostate; and y=relative target volume receiving at least a predetermined level of radiation.

In practice, second input data $y_{in}$ may be in any suitable form, such as a continuous value in relative terms to Y in training data 305, a standard deviation of the distribution of Y, etc. Second input data $y_{in}$ may also be in a "user-friendly" form, such as a discrete classification instruction. In one example, the instruction may be 'emphasize on rectum sparing,' which is then used to derive or determine a quantitative value. For example, using dose estimation model $z = 2.3x_1 - 0.7x_2 + 3.5(y - 0.95)$, rectum sparing may be emphasized by selecting a lower target coverage y<0.95 (e.g., less than 95% receiving at least 45 Gy) to obtain a lower value for z=mean rectum dose. On the other hand, instruction='emphasize on target coverage' will produce the opposite effect.

At 440 in FIG. 4, first input data $x_{in}$ relating to patient geometry of the new patient, and second input data $y_{in}$ relating to treatment planning trade-off are transformed into output data $z_{out}$ using dose estimation model 345. As discussed using FIG. 3, output data $z_{out}$ may express radiation dose in any suitable form, such as DVH, dose distribution, etc. A treatment plan is generated based on output data $z_{out}$ for treatment delivery using any suitable radiotherapy treatment system (see FIG. 5). In practice, estimates produced by dose estimation model 345 may be optimized according to other objectives set by the clinician to produce complete treatment plan.

Figure 5:
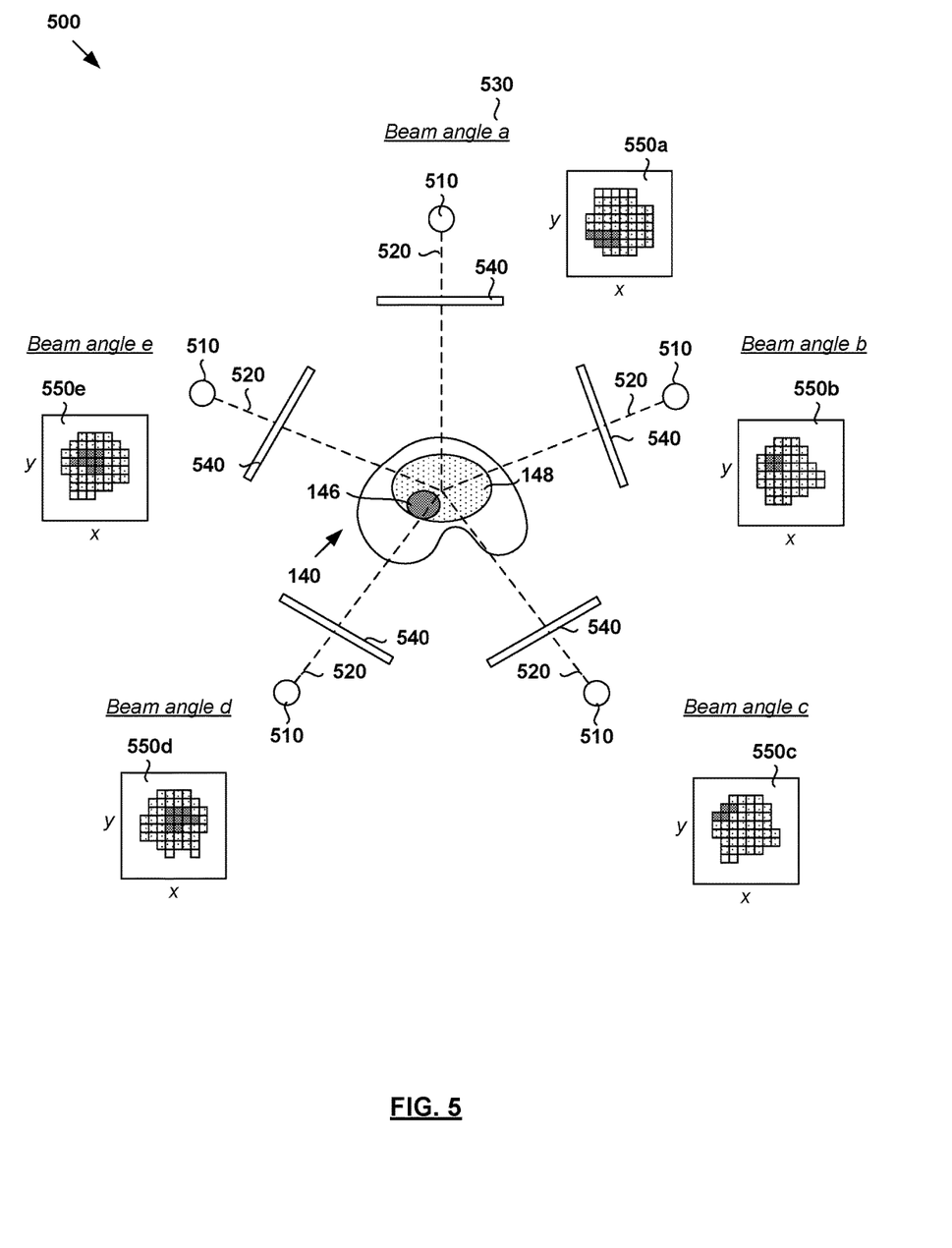
FIG. 5 is a schematic diagram of an example radiotherapy treatment system 500 for treatment delivery according to a treatment plan generated according to the example process in FIG. 4.

FIG. 5 is a schematic diagram of example radiotherapy treatment system 500 for treatment delivery according to a treatment plan generated according to example process 400 in FIG. 4. Although an example is shown in FIG. 5, it will be appreciated any alternative and/or additional configuration may be used depending on the desired implementation. Radiotherapy treatment system 500 includes radiation source 510 to project radiation beam 520 onto treatment volume 140 (see also FIG. 1) representing the patient's anatomy at various beam angles 530.

Although not shown in FIG. 5 for simplicity, radiation source 510 may include a linear accelerator to accelerate radiation beam 520 and a collimator (e.g., multileaf collimator (MLC)) to modify or modulate radiation beam 520. In another example, radiation beam 520 may be modulated by scanning it across a target patient in a specific pattern with various dwell times (e.g., as in proton therapy). A controller (e.g., computer system) may be used to control the operation of radiation source 520 according to treatment plan 160.

During treatment delivery, radiation source 510 may be rotatable (e.g., using a gantry) around a patient, or the patient may be rotated (as in some proton radiotherapy solutions) to emit radiation beam 520 at various beam angles 530 relative to the patient. For example, five equally-spaced beam angles 530 (e.g., angle $\alpha$="a", "b", "c", "d" and "e"; also known as "fields") may be selected for radiation source 510. In practice, any suitable number of beam and/or table or chair angles 530 (e.g., five, seven, nine, etc.) may be selected. At each beam angle 530, radiation beam 520 is associated with fluence plane 540 (also known as an intersection plane) situated outside the patient envelope along a beam axis extending from radiation source 510 to treatment volume 140. As shown, fluence plane 540 is generally at a known distance from the isocenter.

In addition to beam angles 530, fluence parameters of each radiation beam 520 are required for treatment delivery. The term "fluence parameters" may refer generally to characteristics of radiation beam 520, such as its intensity profile as represented using fluence maps (e.g., 550a, 550b, 550c, 550d and 550e for corresponding beam angles 530 "a", "b", "c", "d" and "e"). Each fluence map (e.g., 550a) represents the intensity of radiation beam 520 at each point on fluence plane 540 at a particular beam angle 530 (e.g., "a"). Treatment delivery may then be performed according to fluence maps 550, such as using IMRT, etc. The radiation dose deposited according to fluence maps 550 should, as much as possible, correspond to the treatment plan generated using dose estimation model 345 according to examples of the present disclosure. In practice, fluence maps 550 may be optimized, such as based on the physical characteristics of radiotherapy treatment system 500.

Improvements

In the following, approaches for improving the dose estimation model (e.g., DVH estimation model), and particularly the training data, will be discussed. The approaches below may be used independently from, or together with, the examples described using FIG. 1 to FIG. 5.

(a) Identifying Gaps in Training Data in a Dose Estimation Model

The estimation capability of a dose estimation model often depends on the coverage of the training data. For example, in relation to patient geometry data coverage, a good coverage may lead to, in general, better estimated results for all the anatomical cases that are included in the data range. On the other hand, poor patient geometry data coverage may lead to poorer estimation results for the anatomical cases that fall in the "gap" of missing data.

Unfortunately, the process of generating a dose estimation model is iterative. To generate a dose estimation model, a user (e.g., clinician) often needs to add training cases, analyze and/or verify results of the dose estimation model, add more training cases if necessary (sometimes blindly), and update the dose estimation model. This iterative process is tedious and time-consuming. In some cases, the additional training cases will not help to improve the model results because they are already covered by existing training cases.

To improve the above process, the training data may be automatically analyzed to identify "gaps" or "missing cases" in the training data. This knowledge may then be used to reduce the number of iterations required to improve the results of the dose estimation model. In relation to the patient geometry data, the gaps may be calculated based on a single individual anatomical feature (i.e., 1D-gaps), such as target volume, organ-at-risk (OAR) volume, relative overlap volume, relative out-of-field volume, etc. Multidimensional gaps in patient geometry data may also be identified based on a combination of anatomical features.

There are multiple ways to identify the gaps in any number of dimensions. In one example, a clustering algorithm may be used to identify where the data is clustered, and where the data is lacking by measuring cluster's center and radius in the multiple dimensions. The distance between boundaries of different clusters may then be calculated to identify the gap as, for example, a distance between clusters that is higher than a certain threshold. The threshold may be different for each dimension, or a combination of dimensions. The threshold may also be dependent on the amount of data available or constant. In another example, a simpler approach may be used to determine the gaps in a single dimensionality setting by dividing the data range into multiple parts (e.g., equal parts) and verifying that each part contains at least one data point.

The above approach may be used to improve a dose estimation model in the form of $Z=f1(X)$, where X is a set of feature(s) associated with patient anatomy, Z is a set of feature(s) associated with the estimated radiation dose. Alternatively or additionally, the above approach may be used to improve a dose estimation model in the form of $Z=f2(X, Y)$. As discussed using FIG. 1 to FIG. 5, parameter Y represents a set of feature(s) associated with treatment planning trade-off. In this case, gaps in parameter Y may be identified to improve the coverage of treatment planning trade-off data. Similarly, the gaps may be one- or multidimensional.

Gaps may also be identified in, not only the patient geometry data and trade-off data, but also in other parameters that affect the dose estimation model, such as number of fields, directionality of the fields (angles), etc.

(b) Identifying Candidate Plans for Re-Planning and Trade-Off Plans Using a Dose Estimation Model Conventionally, there is no automatic way to guide a user about "non-optimal" training cases in the input training data. For example, the optimality of a plan may be interpreted as achieving the best OAR sparing possible without compromising the target. A user could try to improve the optimality of the dose estimation model using an iterative process, which includes building the model and re-planning the set of training cases with the current model. However, re-planning all the training cases is time-consuming and inefficient.

To improve the process of generating the dose estimation model, "non-optimal" plans that possibly require a re-plan may be identified, such as after every iteration of model training. In one example, such plans may be identified by comparing the lower and upper DVH estimate mean doses with respect to the clinical DVH mean dose for each OAR and target in a plan. Based on the comparison, the following scenarios may be observed.

In one scenario, if the mean doses for all the OARs fall within the upper and lower estimate mean doses as well as the target mean dose, the plan may be considered of standard quality given the current dose estimation model. In other scenarios, the plan may be worse than expected (indicating a possible re-plan), between than expected, or a mix. In another scenario, if all the OARs have higher mean dose than the lower estimate mean dose, and some have higher mean dose than the upper estimate mean dose and/or the target mean dose is higher than the lower estimate mean dose, it is considered that the plan is a candidate for re-planning (i.e., the plan is worse than expected). In a further scenario, if some OARs mean doses are below the lower mean dose estimate while others are above, the plan is considered to have trade-offs.

Threshold(s) or margin(s) may be set to identify plans that most significantly require re-planning or contain trade-offs more accurately. By identifying plans that require re-planning, the user is guided to focus on what to improve when building the dose estimation model. This way, the user may make more conscious decisions about what to include or exclude from the training set.

Computer System

Figure 6:
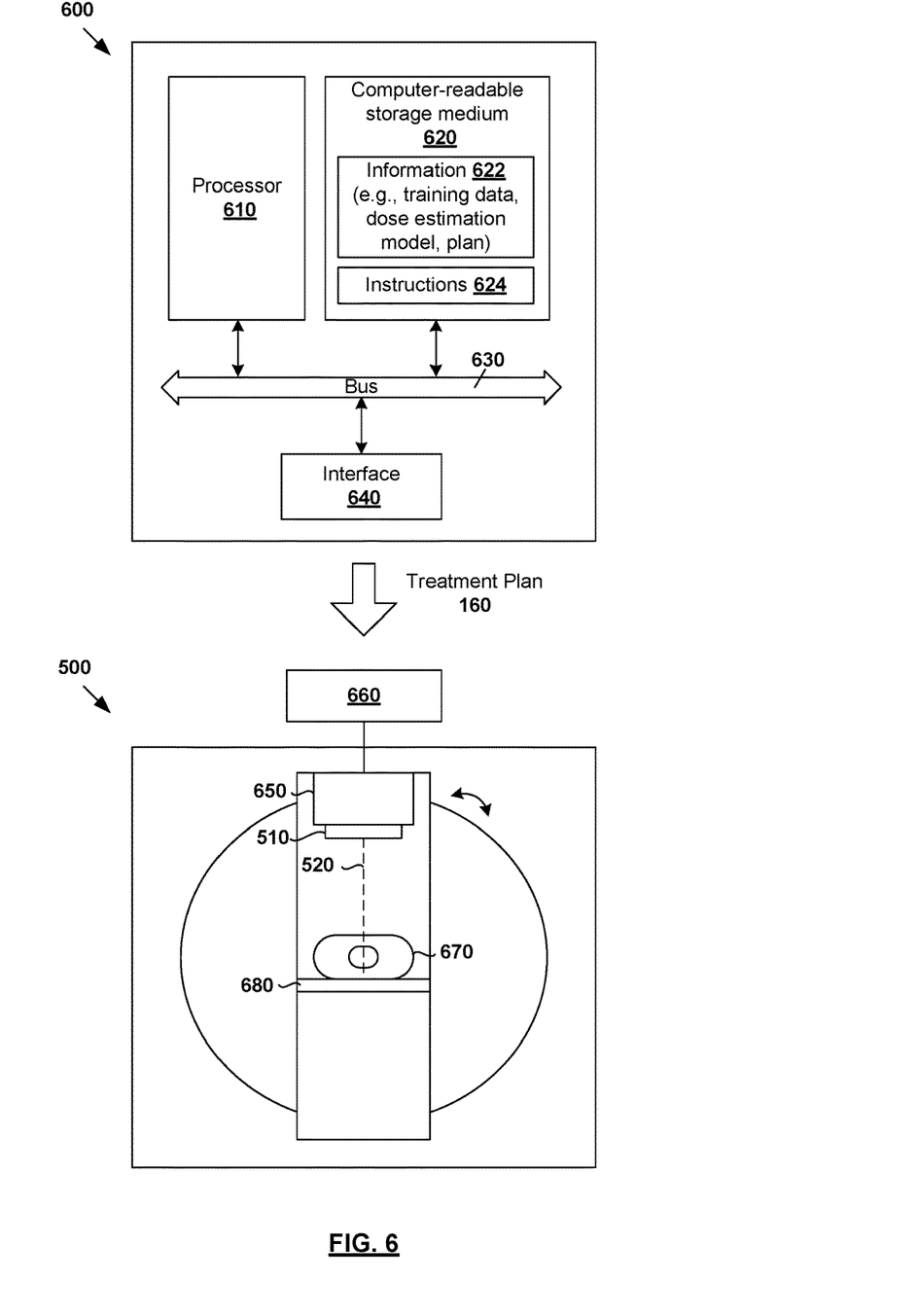
FIG. 6 is a schematic diagram of an example computer system to generate a dose estimation model for radiotherapy treatment planning and an example radiotherapy treatment system for treatment delivery.

The above examples can be implemented by hardware, software or firmware or a combination thereof. FIG. 6 is a schematic diagram of example computer system 600 to generate a dose estimation model for radiotherapy treatment planning and example radiotherapy treatment system 500 for treatment delivery. In this example, computer system 605 (also known as a treatment planning system) may include processor 610, computer-readable storage medium 620, interface 640 to interface with radiotherapy treatment system 500, and bus 630 that facilitates communication among these illustrated components and other components.

Processor 610 is to perform processes described herein with reference to FIG. 1 to FIG. 4. Computer-readable storage medium 620 may store any suitable information 622, such as information relating to training data 305, first data 315, second data 325, third data 335, dose estimation model 345, etc. Computer-readable storage medium 620 may further store computer-readable instructions 624 which, in response to execution by processor 610, cause processor 610 to perform processes described herein.

As explained with reference to FIG. 5, example radiotherapy treatment system 500 may include rotatable gantry 650 to which radiation source 510 is attached. During treatment delivery, gantry 650 is rotated around patient 670 supported on structure 680 to emit radiation beam 520 at various beam angles 530, as explained with reference to FIG. 5. Radiotherapy treatment system 500 may further include controller 660 to obtain (e.g., receive, retrieve from storage, etc.) treatment plan 160 (see also FIG. 1) devised by computer system 605 to control gantry 670, radiation source 510 and radiation beam 520 to deliver radiotherapy treatment.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

We claim:

1. A method for a computer system to generate a dose estimation model for radiotherapy treatment planning, the method comprising:
    obtaining training data that includes multiple treatment plans associated with respective multiple past patients;
    processing the training data to determine, from each of the multiple treatment plans, first data that includes one or more features associated with a particular past patient, second data associated with a treatment planning trade-off between a parameterized first objective and a parameterized second object selected for the particular past patient and third data associated with radiation dose for delivery to the particular past patient;
    generating the dose estimation model by training, based on the first data, the second data and the third data from the multiple treatment plans, the dose estimation model to estimate a relationship that transforms the first data and the second data to the third data;
    obtaining first input data associated with patient geometry of a new patient and second input data associated with a particular treatment planning trade-off selected by a clinician for the new patient; and
    generating a treatment plan for the new patient using the dose estimation model based on the first input data and second input data.

2. The method of claim 1, wherein processing the training data comprises:
    determining, from each of the multiple treatment plans, the second data that is associated with one of the following treatment planning trade-offs:
       trade-off between a first objective associated with an organ-at-risk (OAR) and a second objective associated with a target;
       trade-off between a first objective associated with a first OAR and a second objective associated with a second OAR;
       trade-off between a first objective associated with a target and a second objective associated with multiple OARs;
       trade-off between a first objective associated with a first feature that is non-dosimetrical and a second objective associated with one or more second features; and
       trade-off between a first objective associated with a first group of features and a second objective associated with a second group of features.

3. The method of claim 2, wherein processing the training data comprises:
    determining, from each of the multiple treatment plans, the second data that includes one or more dosimetrical features associated with the first objective or the second objective.

4. The method of claim 2, wherein processing the training data to determine the second data comprises:
    determining, from each of the multiple treatment plans, the second data that includes one or more non-dosimetrical features associated with the first objective or the second objective.

5. The method of claim 1, wherein processing the training data comprises:
    determining, from each of the multiple treatment plans, the first data that includes one or more of the following features associated with patient geometry: target volume, organ-at-risk (OAR) volume, relative overlap volume and relative out-of-field volume; and
    determining, from each of the multiple treatment plans, the third data that includes one or more of the following features associated with radiation dose: dose volume histogram (DVH) and dose distribution.

6. The method of claim 1, wherein training the dose estimation model comprises:
    estimating a first relationship that transforms the first data to the second data; and
    based on the first relationship, estimating the relationship, being a second relationship, that transforms the first data and the second data to the third data.

7. The method of claim 1, wherein obtaining the second input data comprises:
    receiving an instruction associated with the particular treatment planning trade-off; and
    based on the instruction, determining one or more values of the second input data.

8. A non-transitory computer-readable storage medium that includes a set of instructions which, in response to execution by a processor of a computer system, cause the processor to perform a method of generating a dose estimation model for radiotherapy treatment planning, the method comprising:
    obtaining training data that includes multiple treatment plans associated with respective multiple past patients;

processing the training data to determine, from each of the multiple treatment plans, first data that includes one or more features associated with a particular past patient, second data associated with a treatment planning trade-off between a parameterized first objective and a parameterized second object selected for the particular past patient and third data associated with radiation dose for delivery to the particular past patient;

generating the dose estimation model by training, based on the first data, the second data and the third data from the multiple treatment plans, the dose estimation model to estimate a relationship that transforms the first data and the second data to the third data;

obtaining first input data associated with patient geometry of a new patient and second input data associated with a particular treatment planning trade-off selected by a clinician for the new patient; and generating a treatment plan for the new patient using the dose estimation model based on the first input data and second input data.

9. The non-transitory computer-readable storage medium of claim 8, wherein processing the training data comprises:

determining, from each of the multiple treatment plans, the second data that is associated with one of the following treatment planning trade-offs:
  trade-off between a first objective associated with an organ-at-risk (OAR) and a second objective associated with a target;
  trade-off between a first objective associated with a first OAR and a second objective associated with a second OAR;
  trade-off between a first objective associated with a target and a second objective associated with multiple OARs;
  trade-off between a first objective associated with a first feature that is non-dosimetrical and a second objective associated with one or more second features; and
  trade-off between a first objective associated with a first group of features and a second objective associated with a second group of features.

10. The non-transitory computer-readable storage medium of claim 9, wherein processing the training data comprises:

determining, from each of the multiple treatment plans, the second data that includes one or more dosimetrical features associated with the first objective or the second objective.

11. The non-transitory computer-readable storage medium of claim 9, wherein processing the training data to determine the second data comprises:

determining, from each of the multiple treatment plans, the second data that includes one or more non-dosimetrical features associated with the first objective or the second objective.

12. The non-transitory computer-readable storage medium of claim 8, wherein processing the training data comprises:

determining, from each of the multiple treatment plans, the first data that includes one or more of the following features associated with patient geometry: target volume, organ-at-risk (OAR) volume, relative overlap volume and relative out-of-field volume; and determining, from each of the multiple treatment plans, the third data that includes one or more of the following features associated with radiation dose: dose volume histogram (DVH) and dose distribution.

13. The non-transitory computer-readable storage medium of claim 8, wherein training the dose estimation model comprises:

estimating a first relationship that transforms the first data to the second data; and based on the first relationship, estimating the relationship, being a second relationship, that transforms the first data and the second data to the third data.

14. The non-transitory computer-readable storage medium of claim 8, wherein obtaining the second input data comprises:

receiving an instruction associated with the particular treatment planning trade-off; and based on the instruction, determining one or more values of the second input data.

15. A computer system configured to generate a dose estimation model for radiotherapy treatment planning, the computer system comprising:

a processor and a non-transitory computer-readable medium having stored thereon instructions that, when executed by the processor, cause the processor to:

obtain training data that includes multiple treatment plans associated with respective multiple past patients;

process the training data to determine, from each of the multiple treatment plans, first data that includes one or more features associated with a particular past patient, second data associated with a treatment planning trade-off between a parameterized first objective and a parameterized second object selected for the particular past patient and third data associated with radiation dose for delivery to the particular past patient;

generate the dose estimation model by training, based on the first data, the second data and the third data from the multiple treatment plans, the dose estimation model to estimate a relationship that transforms the first data and the second data to the third data;

obtain first input data associated with patient geometry of a new patient and second input data associated with a particular treatment planning trade-off selected by a clinician for the new patient; and generate a treatment plan for the new patient using the dose estimation model based on the first input data and second input data.

16. The computer system of claim 15, wherein the instructions for processing the training data cause the processor to:

determine, from each of the multiple treatment plans, the second data that is associated with one of the following treatment planning trade-offs:
  trade-off between a first objective associated with an organ-at-risk (OAR) and a second objective associated with a target;
  trade-off between a first objective associated with a first OAR and a second objective associated with a second OAR;
  trade-off between a first objective associated with a target and a second objective associated with multiple OARs;
  trade-off between a first objective associated with a first feature that is non-dosimetrical and a second objective associated with one or more second features; and
  trade-off between a first objective associated with a first group of features and a second objective associated with a second group of features.

17. The computer system of claim 16, wherein the instructions for processing the training data cause the processor to:

determine, from each of the multiple treatment plans, the second data that includes one or more dosimetrical features associated with the first objective or the second objective.

18. The computer system of claim 16, wherein the instructions for processing the training data cause the processor to:
determine, from each of the multiple treatment plans, the second data that includes one or more non-dosimetrical features associated with the first objective or the second objective.

19. The computer system of claim 15, wherein the instructions for processing the training data cause the processor to:
determine, from each of the multiple treatment plans, the first data that includes one or more of the following features associated with patient geometry: target volume, organ-at-risk (OAR) volume, relative overlap volume and relative out-of-field volume; and
determine, from each of the multiple treatment plans, the third data that includes one or more of the following features associated with radiation dose: dose volume histogram (DVH) and dose distribution.

20. The computer system of claim 15, wherein the instructions for training the dose estimation model cause the processor to:
estimate a first relationship that transforms the first data to the second data; and
based on the first relationship, estimate the relationship, being a second relationship, that transforms the first data and the second data to the third data.

21. The computer system of claim 15, wherein the instructions for obtaining the second input data cause the processor to:
receive an instruction associated with the particular treatment planning trade-off; and
based on the instruction, determine one or more values of the second input data.

* * * * *